United States Patent [19]

Raghu et al.

[11] Patent Number: 4,459,413
[45] Date of Patent: Jul. 10, 1984

[54] PROCESS FOR PREPARING 5-IMIDAZOLYL KETONES

[75] Inventors: Sivaraman Raghu, Norwalk, Conn.; James Salvatore, Champlain, N.Y.; Steven L. Peake, New Canaan, Conn.

[73] Assignee: American Cyanamid Company, Stamford, Conn.

[21] Appl. No.: 465,732

[22] Filed: Feb. 11, 1983

Related U.S. Application Data

[62] Division of Ser. No. 347,653, Feb. 10, 1982, Pat. No. 4,395,547.

[51] Int. Cl.$^3$ ............................................. C07D 233/64
[52] U.S. Cl. .................................... 548/343; 546/278; 548/336
[58] Field of Search ................. 548/343, 336; 546/278

[56] References Cited

PUBLICATIONS

*Chemical Abstracts*, 82:170937w (1975) [Ger. Offen. 2,430,978, Jorgensen, 1/23/75].
*Chemical Abstracts*, 84:4853m (1976) [Clark, B. et al., *J. Chem. Soc., Perkin Trans IH 1975, (181, 1803–1806*].
*Chemical Abstracts*, 87:53155g (1977) [Bartnik, R. et al., *Rocz. Chem.* 1977, 51(1), 49–57].
*Chemical Abstracts, 87:53156h (1977)* [Ferguson, I., *J. Chem. Soc., Perkin Trans. I* 1977, (6), 672–675].

*Primary Examiner*—Richard A. Schwartz
*Attorney, Agent, or Firm*—Edward A. Conroy, Jr.

[57] ABSTRACT

This disclosure describes a novel process for the preparation of 1-(lower alkyl)substituted derivatives of 6-n-propyl-8-alkylimidazo[1,5-d]-as-triazin-4(3H)-ones which are useful as anti-asthmatic agents.

2 Claims, No Drawings

PROCESS FOR PREPARING 5-IMIDAZOLYL KETONES

This is a division of application, Ser. No. 347,653, filed Feb. 10, 1982, now U.S. Pat. No. 4,395,547.

BRIEF SUMMARY OF THE INVENTION

This invention relates to a novel method for the preparation of 1-(lower alkyl)-6-n-propyl-8-methylimidazo[1,5-d]-as-triazin-4(3H)-ones. More particularly, this invention provides a unique process for the preparation of the corresponding 5-(lower alkanoyl)-4-(lower alkyl)-2-n-propylimidazoles which are the immediate precursors of the 1-(lower alkyl)-6-n-propyl-8-(lower alkyl)imidazo[1,5-d]-as-triazin-4(3H)-ones. The final products of the novel process of the present invention are highly useful for meliorating asthma and for inhibiting diesterase in mammals. They inhibit the release of mediators (to the extent of 50%) from the human basophil at 13μM concentration and also protect guinea pigs from anaphylactic shock. In the mouse, they are active both orally and intraperitoneally in inhibiting passive cutaneous anaphylaxis.

The steps involved in the novel process of the present invention may be depicted as follows:

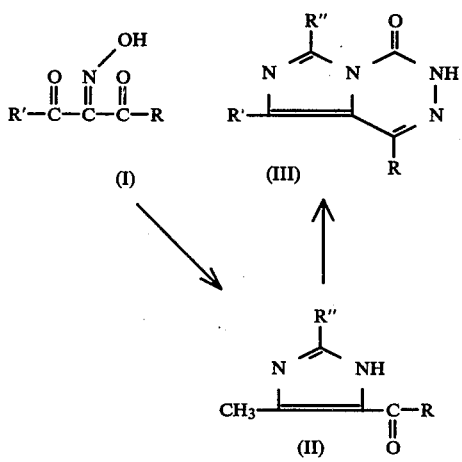

wherein R and R' are methyl, ethyl or n-propyl.

DETAILED DESCRIPTION OF THE INVENTION

The starting material for the novel process of the present invention is α-oximino-β-diketone (I) which is condensed with commercially available 2-aminovaleric acid or its esters. This condensation is conveniently carried out in a suitable inert solvent (e.g., acetonitrile, propionitrile, 2-methoxyethanol, 2-ethoxyethanol, dimethoxyethane, n-butanol DMF, toluene) at the reflux temerature (80°-135° C.) for a period of time of from about two to about 24 hours. The conversion of the 2-n-propyl-4-alkyl-5-imidazolyketones (II) to the corresponding 1-(lower alkyl)-6-n-propyl-8-(lower alkyl)imidazo[1,5-d]-as-triazin4(3H)-ones (III) is carried out as set forth in the following reaction scheme:

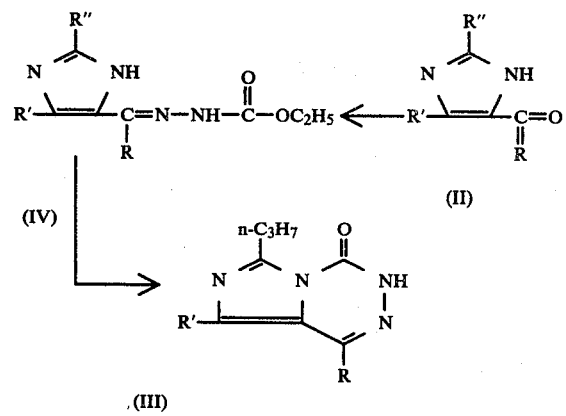

wherein R is as hereinbefore defined. In accordance with the above reaction scheme, condensation of (II) with ethyl carbazate in n-butanol or diphenyl ether under reflux for several hours provides (IV) which may be isolated by evaporation of the reaction solvent. Cyclization of (IV) is accomplished in diphenyl ether at 150°-250° C. for 15-45 minutes to provide the compounds (III). Isolation of (III) is achieved by dilution of the reaction mixture with petroleum ether or by extraction of the reaction mixture with 10% aqueous hydrochloric acid. The acid extract is neutralized with potassium carbonate and the product extracted with solvents such as chloroform or ethyl acetate.

The invention will be described in greater detail in conjunction with the following specific examples.

EXAMPLE 1

5-Acetyl-4-methyl-2-n-propylimidazole

To 40 g (0.309 moles) of 3-oximino-2,4-pentanedione dissolved in 200 ml of n-butanol was added 39.92 g (0.341 moles) of d,1-norvaline. The resulting mixture was brought to reflux, while stirring rapidly under nitrogen with an oil bath. After 19.3 h the reaction mixture was cooled, and then suction filtered. The residue was washed with ethyl acetate (100 ml) and the combined filtrates concentrated in vacuo. The resulting oil was dissolved in ethyl acetate (200 ml) and extracted with three 50 ml portions of 5% aqueous sodium hydroxide solution. Removal of the solvent in vacuo gave 0.15 moles (55.7% yield based on recovered d,1-norvaline) of 5-acetyl-4-methyl-2-propylimidazole.

EXAMPLE 2

5-Acetyl-4-methyl-2-n-propylimidazole

An acetonitrile (250 ml) mixture of 3-oximino-2, 4-pentanedione (40 g, 0.31 moles) and d,1-norvaline (43.55 g, 0.372 moles) was heated to reflux under nitrogen. After 23.7 h the reaction mixture was allowed to cool, then suction filtered. The residue was washed with acetonitrile and the combined filtrates concentrated in vacuo. After dissolving the resulting oil in ethyl acetate (100 ml), it was washed with three 40 ml portions of 5% aqueous sodium hydroxide solution. The combined organic extracts were dried over anhydrous potassium carbonate and then concentrated in vacuo to give 0.1 moles (43.5% yield based on recovered d,1-norvaline) of 5-acetyl-4-methyl-2-propylimidazole.

EXAMPLE 3

5-Acetyl-4-methyl-2-n-propylimidazole

To 40 g (0.31 moles) of 3-oximino-2,4-pentanedione dissolved in 297 ml of acetonitrile was added 40.64 g (0.31 moles) of methyl d,1-norvaline. The reaction mixture was refluxed 21.2 h under nitrogen, cooled, then concentrated in vacuo. The resulting oil was dissolved in 50 ml of ethanol and 140 ml of 10% aqueous sodium hydroxide. After 4 h of reflux, the cooled mixture was extracted with ethyl acetate (900 ml total) and dried over anhydrous sodium sulfate. Removal of the solvent in vacuo afforded 0.16 moles (51% yield) of 5-acetyl-4-methyl-2-propylimidazole.

EXAMPLE 4

5-Acetyl-4-methyl-2-ethylimidazole

To 4.78 g (0.037 moles) of 3-oximino-2,4-pentanedione dissolved in 40 ml of acetonitrile was added 3.82 g (0.037 moles) of 2-aminobutyric acid. The mixture was brought to reflux, while stirring rapidly under nitrogen, with an oil bath. After 22.5 h the reaction mixture was cooled, suction filtered, and the residue washed with acetonitrile (50 ml). The combined filtrates were concentrated in vacuo, and the resulting oil dissolved in 1 M hydrochloric acid (30 ml). The acid solution was washed with methylene chloride (4×20 ml), then neutralized with solid potassium carbonate. Extraction with methylene chloride, followed by drying over anhydrous potassium carbonate and concentration in vacuo furnished 0.021 moles (67.8%) yield based on recovered d,l-norvaline) of 5-acetyl-2-ethyl-4-methylimidazole.

EXAMPLE 5

5-Acetyl-4-methyl-2-ethylimidazole

To 4.99 g (0.039 moles) of 3-oximino-2,4-pentanedione dissolved in acetonitrile (40 ml) was added 4.59 ml (0.039 moles) of methyl 2-aminobutyrate. After stirring for two hours at room temperature, then at reflux for 2.5 h , the reaction mixture was cooled and treated with 15 ml of ethanol and 15 ml of 10% aqueous sodium hydroxide. The resulting mixture was refluxed for 3.8 h, cooled, then extracted with ethyl acetate. The combined organic extracts were dried over anhydrous sodium sulfate, then concentrated in vacuo to give 0.024 moles (62% yield) of 5-acetyl-2-ethyl-4-methylimidazole.

EXAMPLE 6

5-Acetyl-4-phenyl-2-ethylimidazole

An acetonitrile solution (15 ml) of 2-oximino-1-phenyl-1,3-butanedione (1.38 g, 7.22 mmoles) and methyl 2-aminobutyrate (0.85 ml, 7.22 mmol) was refluxed under nitrogen for 26.4 h. After concentrating the cooled reaction mixture, the residue was dissolved in 10 ml of ethanol and 20 ml of 10% aqueous sodium hydroxide. This mixture was refluxed 4.9 h, cooled, then extracted with ethyl acetate. Removal of the solvent in vacuo gave 0.65 g (42% yield) of 5-benzoyl-2-ethyl-4-methylimidazole and 5-acetyl-2-ethyl-4-phenylimidazole (86:14 respectively).

EXAMPLE 7

5-Propionyl-4-methyl-2-n-propylimidazole

To 92.4 g (0.646 moles) of 3-oximino-2,4-hexanedione dissolved in 807 ml of n-butanol was added 90.75 g (0.775 moles) of d,l-norvaline. The mixture was refluxed 6.25 h, then cooled and concentrated in vacuo. The residue was taken up in ethyl acetate (500 ml), suction filtered and the filtrate washed with 10% aqueous sodium hydroxide (4×100 ml). Removal of the solvent in vacuo gave 0.29 moles (48% yield based on recovered amino acid) of 4-methyl-5-propinoyl-2-propylimidazole and 5-acetyl-4-methyl-2-propylimidazole (87:13 respectively).

EXAMPLE 8

5-Benzoyl-4-phenyl-2-n-propylimidazole

The substitution of 1,3-diphenyl-2-oximino-1,3-propanedione for 3-oximino-2,4-pentanedione in example 1 affords 5-benzoyl-4-phenyl-2-propylimidazole.

EXAMPLE 9

5-Isobutyryl-4-isopropyl-2-n-propylimidazole

The substitution of 2,6-dimethly-4-oximino-3,5- heptanedione for 3-oximino-2,4-pentanedione in example 1 affords 4-isopropyl-5-(2-methylpropionyl)-2-propylimidazole.

EXAMPLE 10

5-Propionyl-4-ethyl-2-n-propylimidazole

The substitution of 4-oximino-3,5-heptanedione for 3-oximino-2,4-pentanedione in example 1 affords 4-ethyl-5-propinoyl-2-propylimidazole.

EXAMPLE 11

5-Isovaleryl-4-isobutyl-2-n-propylimidazole

The substitution of 2,8-dimethyl-5-oximino-4,6-nonanedione for 3-oximino-2,4-pentanedione in example 1 affords 4-isobutyl-5-(3-methylbutyroyl)-2-propylimidazole.

EXAMPLE 12

5-Isovaleryl-4-methyl-2-n-propylimidazole

The substitution of 6-methyl-3-oximino-2,4-heptanedione for 3-oximino-2,4-hexanedione in example 7 forms 4-methyl-5-(3-methylbutyroyl)-2-propylimidazole.

EXAMPLE 13

5-Hexanoyl-4-methyl-2-n-propylimidazole

The substitution 3-oximino-2,4-nonanedione for 3-oximino-2,4-hexanedione in example 7 forms 5-hexanoyl-4-methyl-2-propylimidazole.

EXAMPLE 14

5-Phenylacetyl-4-methyl-2-n-propylimidazole

The substitution of 3-oximino-1-phenyl-2,4-pentanedione for 3-oximino-2,4-hexanedione in example 7 forms 4-methyl-5-(1-phenylacetyl)-2-propylimidazole.

EXAMPLE 15

5-Acetyl-4-methylimidazole

The substitution of glycine for d,l-norvaline in example 1 gives 5-acetyl-4-methylimidazole.

EXAMPLE 16

5-Acetyl-2,4-dimethylimidazole

The substitution of d,l-alanine for d,l-norvaline in example 1 gives 5-acetyl-2,4-dimethylimidazole.

EXAMPLE 17

5-Acetyl-4-methyl-2-isopropylimidazole

The substitution of d,l-valine for d,l-norvaline in example 1 gives 5-acetyl-2-isopropyl-4-methylimidazole.

EXAMPLE 18

5-Acetyl-4-methyl-2-isobutylimidazole

The substitution of d,l-leucine for d,l-norvaline in example 1 gives 5-acetyl-2-isobutyl-4-methylimidazole.

EXAMPLE 19

5-Acetyl-4-methyl-2-benzylimidazole

The substitution of d,l-phenylalanine for d,l-norvaline in example 1 gives 5-acetyl-2-benzyl-4methylimidazole.

EXAMPLE 20

5-Acetyl-4-methyl-2-vinylimidazole

An acetonitrile solution of allylamine (0.4 g, 7.8 mmol) and 3-oximino-2,4-pentanedione (1 g, 7.8 mmol) was refluxed for 6 hours. The acetonitrile was evaporated to give 0.9 g of 5-acetyl-4-methyl-2-vinylimidazole.

EXAMPLE 21

5-Acetyl-4-methyl-2-(2-furyl)imidazole

The substitution of furfurylamine for allylamine in example 20 affords 5-acetyl-2-(2-furyl)-4-methylimidazole.

EXAMPLE 22

5-Acetyl-4-methyl-2-(3-pyridyl)imidazole

The substitution of 3-picolylamine for allylamine in example 20 gives 5-acetyl-4-methyl-2-(3-pryridyl) imidazole.

EXAMPLE 23

9-(5-Acetyl-4-methylimidazol-2-yl)anthracene

The substitution of 9-(aminomethyl)-anthracene for allylamine in Example 20 gives 9-(5-acetyl-4-methylimidazo -2-yl)anthracene.

EXAMPLE 24

2-(5-Acetyl-4-methylimidazol-2-yl)benzimidazole

The substitution of 2-(aminomethyl)benzimidazole for allylamine in example 20 affords 2-(5-acetyl-4-methylimidazo-2-yl)benzimidazole.

EXAMPLE 25

5-Carbethoxy-4-methyl-2-n-propylimidazole

The substitution of ethyl 2-oximino-3-ketobutrate for 3-oximino-2,4-pentanedione in Example 1 affords 5-carboethoxy-4-methyl-2-propylimidazole.

EXAMPLE 26

1,8-Dimethyl-6-n-propylimidazo[1,5-d]-as-triazin-4(3H)-one

A mixture of 59.7 g. of methyl 2-n-propyl-4--methyl-5-imidazolyl ketone, 41.14 g. of ethyl carbazate, 200 ml. of n-butanol and 4 drops of glacial acetic acid is warmed until solution is complete and then heated under reflux for 5 hours. The solution is concentrated in vacuo to an oily residue, 250 ml. of diphenyl ether are added and the resulting solution is heated with stirring in an oil bath for 30 minutes after the start of gas evolution. The temperature is maintained as closely as possible to the point at which gas evolution starts (150°–250° C.). The reaction is removed from the oil bath, cooled to 50° C. and diluted with 1–2 volumes hexane. The product is collected, washed with petroleum ether and then dissolved in 200 ml. of chloroform. This solution is filtered through 250 ml. of Magnesol ® followed by an 800 ml. chloroform wash. The filtrate is concentrated in vacuo and the residue is recrystallized from 250 ml. of ethyl acetate, giving 48.2 g. of the desired product as off-white crystals, m.p. 154°–155° C.

EXAMPLE 27

1-Ethyl-6-n-propyl-8-methylimidazo-[1,5-d]-as-triazin-4(3H)-one

The procedure of Example 26 was repeated using ethyl 2-n-propyl-4-methyl-5-imidazolyl ketone in place of the methyl 2-n-propyl-4-methyl-5-imidazolyl ketone of that example whereby the title product, m.p. 147°–150° C., was obtained.

EXAMPLE 28

1,6-Di-n-propyl-8-methylimidazo-[1,5-d]-as-triazin-4(3H)-one

The procedure of Example 26 was repeated using n-propyl 2-n-propyl-4-methyl-5-imidazolyl ketone in place of the methyl 2-n-propyl-4-methyl-5-imidazolyl ketone of that example whereby the title product, m.p. 145°–146° C., was obtained.

EXAMPLE 29

1,8-Dimethyl-6-n-propylimidazo[1,5-d-]-as-triazin-4(3H)-one, monohydrate, monohydrochloride A 10.0 g. portion of 1,8-dimethyl-6-n-propylimidazo[1,5-d]-as-triazin-4(3H)-one was dissolved in 800 ml. of dichloromethane and treated with a stream of hydrogen chloride gas over a 30 minute period. The resulting precipitate was collected, slurried with two 60 ml. portions of dichloromethane and then dried in vacuo, giving 10.6 g. of the desired product as a white solid, m.p. 249°–255° C.

EXAMPLE 30

1-Ethyl-6-n-propyl-8-methylimidazo[1,5-d]-as-triazin-4(3H)-one, monohydrate, monohydrochloride The procedure of Example 29 was repeated using 1-ethyl-6-n-propyl-8-methylimidazo[1,5-d]-as-triazin-4-(3H)-one in place of 1,8-dimethyl-6-n-propylimidazo[1,5-d]-as-triazin-4(3H)-one and giving the desired product, m.p. 236°–243° C.

EXAMPLE 31

1,6-Di-n-propyl-8-methylimidazo[1,5-d]-as-triazin-4(3H)-one, monohydrate, monohydrochloride The procedure of Example 29 was repeated using 1,6-di-n-propyl-8-methylimidazo[1,5-d]-as-triazin-4(3H)-one in place of 1,8-dimethyl-6-n-propylimidazo[1,5-d]-as-triazin-4(3H)-one and giving the desired product, m.p. 225° C. (dec.).

EXAMPLE 32

1-Methyl-6-n-propyl-8-ethylimidazo-[1,5-d]-as-triazin-4(3H)-one

The procedure of Example 26 was repeated using methyl 2-n-propyl-4-ethyl-5-imidazoyl ketone in place of the methyl 2-n-propyl-4-methyl-5-imidazoyl ketone of that example whereby the title product was obtained.

EXAMPLE 33

1-Methyl-6-n-propyl-8-ethylimidazo[1,5-d]-as-triazin-4(3H)-one, monohydrate, monohydrochloride.

The procedure of Example 29 was repeated using 1-methyl-6-n-propyl-8-ethylimidazo-[1,5-d]-as-triazin-4(3H)-one in place of 1,8-dimethyl-6-n-propylimidazo-[1,5-d]-as-triazin-4(3H)-one.

We claim:

1. The process of preparing the 5-imidazolyl ketones of the formula:

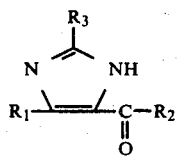

wherein $R_1$ is alkyl having up to 3 carbon atoms or phenyl; $R_2$ is alkyl having up to 5 carbon atoms, benzyl or phenyl; and $R_3$ is hydrogen, alkyl, aryl or heterocyclic having up to 14 carbon atoms or benzyl which comprises condensing a β-oximino-α,γ-alkanedione of the formula:

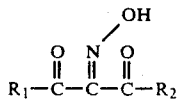

wherein $R_1$ and $R_2$ are as hereinabove defined with an aminoacid or ester of the formula:

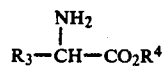

wherein $R_3$ is as hereinabove defined and $R_4$ is hydrogen or lower alkyl in an inert solvent at from about 80° C. to about 135° C. for a period of time of from about two hours to about 24 hours.

2. The process of preparing the 5-imidazolyl ketones of the formula:

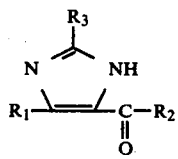

wherein $R_1$, $R_2$ and $R_3$ are each individually selected from the group consisting of methyl, ethyl, n-propyl and isopropyl which comprises condensing a β-oximino-α, γ-alkanedione of the formula:

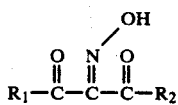

wherein $R_1$ and $R_2$ are as hereinabove defined with an α-aminoacid or ester of the formula:

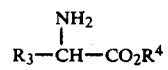

wherein $R_3$ is as hereinabove defined and $R_4$ is hydrogen, methyl, ethyl, n-propyl or isopropyl in an inert solvent at from about 80° C. to about 135° C. for a period of time of from about two hours to about 24 hours.

* * * * *